(12) United States Patent
Janzen et al.

(10) Patent No.: US 12,653,206 B2
(45) Date of Patent: Jun. 16, 2026

(54) LACTIC ACID BACTERIAL STRAIN WITH IMPROVED TEXTURIZING PROPERTIES

(71) Applicant: Chr. Hansen A/S, Hoersholm (DK)

(72) Inventors: Thomas Janzen, Hoersholm (DK); Ditte Ellegaard Christiansen, Hoersholm (DK); Jesper Broend, Hoersholm (DK); Victoria Prebner, Hoersholm (DK)

( * ) Notice: Subject to any disclaimer, the term of this patent is extended or adjusted under 35 U.S.C. 154(b) by 337 days.

(21) Appl. No.: 18/253,180

(22) PCT Filed: Nov. 16, 2021

(86) PCT No.: PCT/EP2021/081821
§ 371 (c)(1),
(2) Date: May 16, 2023

(87) PCT Pub. No.: WO2022/106405
PCT Pub. Date: May 27, 2022

(65) Prior Publication Data
US 2024/0008502 A1    Jan. 11, 2024

(30) Foreign Application Priority Data
Nov. 17, 2020    (EP) ..................................... 20208145

(51) Int. Cl.
| | |
|---|---|
| *A61K 39/02* | (2006.01) |
| *A23C 9/123* | (2006.01) |
| *C12N 1/205* | (2026.01) |
| *C12R 1/46* | (2006.01) |

(52) U.S. Cl.
CPC ............ *A23C 9/1238* (2013.01); *C12N 1/205* (2021.05); *C12R 2001/46* (2021.05)

(58) Field of Classification Search
None
See application file for complete search history.

(56) References Cited

U.S. PATENT DOCUMENTS

| | | | |
|---|---|---|---|
| 8,865,238 | B2 | 10/2014 | Janzen et al. |
| 9,060,524 | B2 | 6/2015 | Janzen et al. |
| 9,416,351 | B2 | 8/2016 | Janzen et al. |
| 9,562,221 | B2 | 2/2017 | Janzen et al. |
| 9,777,253 | B2 | 10/2017 | Folkenberg et al. |
| 11,272,716 | B2 | 3/2022 | Derkx et al. |
| 2017/0096635 | A1 | 4/2017 | Janzen et al. |

FOREIGN PATENT DOCUMENTS

| | | |
|---|---|---|
| WO | WO-2011/092300 A1 | 8/2011 |
| WO | WO-2011/161085 A1 | 12/2011 |
| WO | WO-2018/041717 A1 | 3/2018 |

OTHER PUBLICATIONS

Shu et al (Emirates J. Food and Agriculture. 2017. 29(4): 256-263).*
Turner, Mark S. et al.; "Inactivation of an Iron Transporter in *Lactococcus lactis* Results in Resistance to Tellurite and Oxidative Stress"; Applied and Environmental Microbiology, vol. 73, No. 19; Oct. 2007; pp. 6144-6149.

* cited by examiner

*Primary Examiner* — Jennifer E Graser
(74) *Attorney, Agent, or Firm* — Yoshimi D. Barron

(57) ABSTRACT

The present invention relates to a novel *Streptococcus thermophilus* strain having improved texturizing properties, compositions comprising said strain as well as fermented products manufactured using said strain.

20 Claims, No Drawings

LACTIC ACID BACTERIAL STRAIN WITH IMPROVED TEXTURIZING PROPERTIES

CROSS-REFERENCE TO RELATED APPLICATIONS

The present application is the U.S. National Stage of International Application No. PCT/EP2021/081821, filed Nov. 16, 2021, and claims priority to European Patent Application No. 20208145.1, filed Nov. 17, 2020.

TECHNICAL FIELD OF THE INVENTION

The present invention relates to a mutant of *Streptococcus thermophilus*, which was found to have improved texturizing properties while essentially maintaining the properties of its parent strain. The present invention, furthermore, relates to compositions, such as a starter culture, comprising the mutant and to fermented products made using this mutant.

BACKGROUND OF THE INVENTION

The food industry use numerous bacteria, in particular lactic acid bacteria, in order to improve the taste and the texture of foods but also in order to extend the shelf life of these foods. In the case of the dairy industry, lactic acid bacteria are used intensively in order to bring about the acidification of milk (by fermentation) but also in order to texturize the product into which they are incorporated.

Among the lactic acid bacteria (LAB) used in the food industry, *Streptococcus, Lactococcus, Lactobacillus, Leuconostoc, Pediococcus* and *Bifidobacterium* are predominantly applied. The lactic acid bacteria of the species *Streptococcus thermophilus* (*S. thermophilus*) are used extensively alone or in combination with other bacteria such as *Lactobacillus delbrueckii* subsp *bulgaricus* (*L. bulgaricus*) for the production of food products, in particular fermented products. They are used in particular in the formulation of the ferments used for the production of fermented milks, for example yoghurts. Certain of them play a dominant role in the development of the texture of the fermented product. This characteristic is closely linked to the production of extracellular polymeric that are secreted by the lactic acid bacteria into the surrounding environment.

The current trend in yoghurt is for mild flavor and high texture. Today this is achieved by the use of cultures which produce a mild flavor and the addition of thickeners or protein to give the desired thickness. Yoghurt producers would like to be able to make yoghurt with these properties without the addition of thickening agents. This will help them reduce cost and give a cleaner label. One very attractive way to achieve this would be to have a starter culture which produces a high level of texture.

Some LAB strains contribute significantly to an improved texture associated with their ability to produce exo- (or extracellular) polysaccharides (EPS), which can be capsular (remain attached to the cell in the form of capsules) or secreted into the media. EPS consists of either a single type of sugar (homo-exopolysaccharides) or repeating units made of different sugars (hetero-exopolysaccharides). EPS-producing LAB are of interest, since EPS act as natural viscosifiers and texture enhancers of fermented foods. Furthermore, EPS from food-grade LAB with defined rheological properties have potential for development and exploitation as food additives. EPS are known to improve the rheological properties of LAB-fermented products by influencing viscosity, syneresis, firmness and sensory properties. The primary structural features (monosaccharide type and configuration, glycosidic linkage, non-sugar decorations, charge), the conformation and molecular weight, the amount of polysaccharide and the interactions of the polysaccharide with other system components are all factors that can contribute to and influence the displayed techno-functional properties (Zeidan et al., 2017 FEMS Microbiol Rev 41: 168-200).

Although the presence of exopolysaccharide does not confer any obvious advantage to growth or survival of *S. thermophilus* in milk, in situ production by this species or other dairy lactic acid bacteria typically imparts a desirable "ropy" or viscous texture to fermented milk products. Work has also shown that exopolysaccharide-producing *S. thermophilus* can enhance the functional properties of Mozzarella cheese. For further details see the review article of Broadbent et al. (J. dairy Sci. 86:407-423).

In order to meet the requirements of the industry, it has become necessary to provide novel texturizing strains of lactic acid bacteria, in particular of *S. thermophilus*, for texturizing food products. Especially there is a need for novel texturizing strains of *S. thermophilus* which can be used together with texturizing strains of *Lactobacillus delbrueckii* subsp *bulgaricus*.

SUMMARY OF THE INVENTION

The present invention relates to a novel *Streptococcus thermophilus* strain having improved properties in particular in relation to its ability to improve texture of fermented dairy products such as e.g. yogurt and which is useful in present-day highly industrialized dairy production.

In particular, the present invention discloses a novel *S. thermophilus* strain DSM 33676.

Thus, an aspect of the present invention relates to *S. thermophilus* strain DSM 33676 and mutants and variants thereof.

In another aspect the present invention relates to a composition comprising the *S. thermophilus* strain DSM 33676.

In a further aspect the present invention relates to a method of producing a fermented product, comprising fermenting a substrate with the *S. thermophilus* strain DSM 33676 or a composition comprising *S. thermophilus* strain DSM 33676.

In yet another aspect the present invention relates to a fermented product obtainable by the method of the present invention.

In another aspect the present invention relates to a fermented product comprising the *S. thermophilus* strain DSM 33676.

Following this, a further aspect relates to the use of the *S. thermophilus* strain DSM 33676 for the manufacture of a fermented product.

DETAILED DESCRIPTION OF THE INVENTION

Definitions

Prior to outlining the present invention in more details, a set of terms and conventions is first defined:

The term "milk" is to be understood as the lacteal secretion obtained by milking any mammal, such as cows, sheep, goats, buffaloes or camels. In a preferred embodiment, the milk is cow's milk. The term milk also includes protein/fat solutions made partly or exclusively of plant materials.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder or the milk substrate may originate from a plant material.

Preferably, at least part of the protein in the milk substrate is (i) proteins naturally occurring in mammalian milk, such as casein or whey protein or (ii) proteins naturally occurring in plant milk. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a fermented product such as a dairy or non-dairy product in solid or liquid form (fermented milk product).

In the present context the term "starter culture" is a culture which is a preparation of one or more bacterial strains (such as lactic acid bacteria strains) to assist the beginning of the fermentation process in preparation of fermented products such as various foods, feeds and beverages.

In the present context, a "yoghurt starter culture" is a bacterial culture which comprises at least one *Lactobacillus delbrueckii* subsp *bulgaricus* (*L. bulgaricus*) strain and at least one *Streptococcus thermophilus* (*S. thermophilus*) strain. In accordance herewith, a "yoghurt" refers to a fermented milk product obtainable by inoculating and fermenting a milk substrate with a composition comprising a *L. bulgaricus* strain and a *S. thermophilus* strain.

The term "Tellurite resistant" is understood a bacterial strain which is able to grow (form a colony) on M17 agar plates containing 0.1 mM K2Te03 after 1 to 3 days of incubation at 37° C.

In the present context, the term "mutant" should be understood as a strain derived, or a strain which can be derived from a strain of the invention (or the mother strain) by means of e.g. genetic engineering, radiation and/or chemical treatment. The mutant can also be a spontaneously occurring mutant. It is preferred that the mutant is a functionally equivalent mutant, e.g. a mutant that has substantially the same, or improved, properties (e.g. regarding viscosity, gel firmness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than less than 0.001% or even less than 0.0001% of the nucleotides in the bacterial genome have been replaced with another nucleotide, or deleted, compared to the mother strain.

In the present context, the term "variant" should be understood as a strain which is functionally equivalent to a strain of the invention, e.g. having substantially the same, or improved, properties e.g. regarding viscosity, gel stiffness, mouth coating, flavor, post acidification, acidification speed, and/or phage robustness). Such variants, which may be identified using appropriate screening techniques, are a part of the present invention.

Novel *Streptococcus thermophilus* Strain and Applications Thereof.

The inventors have surprisingly identified a *S. thermophilus* strain (i.e. DSM 33676) that fulfils the needs of the industry. The new strain shows improved rheological properties, such a texturization, when applied alone or as part of a mixed culture in a dairy substrate when compared to its mother strain. *S. thermophilus* strain DSM 33676 have the capacity to be used in e.g. dairy cultures such as yoghurt cultures to obtain improved rheological parameters such as shear stress and gel stiffness of the final product.

Thus, on one aspect of the invention relates to a *Streptococcus thermophilus* strain DSM 33676 and mutants and variants thereof.

It is contemplated that the mutants and variants show the same or similar shear stress and/or gel firmness characteristics as DSM 33676. In the present context the term "similar shear stress" is to be understood as a range spanning from 10% below the shear stress characteristics of DSM 33676 to 10% above the shear stress characteristics of DSM 33676, the range may also be 9% below/above the shear stress characteristics of DSM 33676, such as 8% below/above of the shear stress characteristics of DSM 33676, e.g. 7% below/above of the shear stress characteristics of DSM 33676, such as 6% below/above of the shear stress characteristics of DSM 33676, e.g. 5% below/above of the shear stress characteristics of DSM 33676, such as 4% below/above of the shear stress characteristics of DSM 33676, e.g. 3% below/above of the shear stress characteristics of DSM 33676, such as 2% below/above of the shear stress characteristics of DSM 33676 or 1% below/above of the shear stress characteristics of DSM 33676.

In the present context the term "similar gel firmness" is to be understood as a range spanning from 10% below the gel firmness characteristics of DSM 33676 to 10% above the gel firmness characteristics of DSM 33676, the range may also be 9% below/above the gel firmness characteristics of DSM 33676, such as 8% below/above of the gel firmness characteristics of DSM 33676, e.g. 7% below/above of the gel firmness characteristics of DSM 33676, such as 6% below/above of the gel firmness characteristics of DSM 33676, e.g. 5% below/above of the gel firmness characteristics of DSM 33676, such as 4% below/above of the gel firmness characteristics of DSM 33676, e.g. 3% below/above of the gel firmness characteristics of DSM 33676, such as 2% below/above of the gel firmness characteristics of DSM 33676 or 1% below/above of the gel firmness characteristics of DSM 33676.

In the above "characteristics" is to be understood in the context of the definition part where it's stated how to appropriately measure shear stress or gel firmness.

Methods for determining the texture of fermented products such as dairy products include measuring the shear stress (viscosity) or gel stiffness (complex modulus) of the fermented product and are readily available and known in the art and exemplified herein.

In one embodiment of the present inventio the *Streptococcus thermophilus* strain DSM 33676 generates a shear stress greater than 20 Pa measured as shear stress in 300 1/s (Pa) after 16 hours of growth in in skimmed milk (0.5% fat) at 43° C. when inoculated in an amount of at least $10^7$ cells per ml of milk.

A shear stress greater than 20 Pa, 22 Pa, 24 Pa, 26 Pa, 28 Pa, 30, 31 Pa, 32 Pa, 33 Pa, 34 Pa, or 35 Pa at 300 s$^{-1}$ when measured on a fermented product made by addition of DSM 33676 may be desired. Shear stress is measured as described above. Shear stress of a single culture is measured in Example 2.

A shear stress greater than 35 Pa, 40 Pa, 45 Pa, 50 Pa, 60 Pa, 70 Pa, 80 Pa, 90 Pa, or 100 Pa at 300 s$^{-1}$ when measured on a fermented product made by addition of a composition of DSM 33676 and at least one further lactic acid bacteria strain (mixed culture) may be desired as this resembles a sensory viscosity/mouth thickness which is preferred by a sensory panel. Shear stress is measured as described above. Shear stress is measured as described in example 3.

In one embodiment of the present invention the *Streptococcus thermophilus* strain DSM 33676 generates a complex modulus greater than 89 Pa when measured by oscillation at 1.52 Hz after 16 hours of growth in in skimmed milk (0.5% fat) at 43° C. when inoculated in an amount of at least $10^7$ cells per ml of milk.

A complex modulus greater than 90 Pa, 91 Pa, 92 Pa, 93 Pa, 94 Pa, 95, 96 Pa, 97 Pa, 98 Pa, 99 Pa, or 100 Pa when measured by oscillation at 1.52 Hz on a fermented product made by addition of DSM 33676 may be desired. Complex modulus is measured as described above. Complex modulus of a single culture is measured in Example 2.

A complex modulus greater than 140 Pa, 141 Pa, 142 Pa, 143 Pa, 144 Pa, 145 Pa, 146 Pa, 147 Pa, or 147 Pa when measured by oscillation at 1.52 Hz on a fermented product made by addition of a composition of DSM 33676 and at least one further lactic acid bacteria strain (mixed culture) may be desired as this resembles a sensory viscosity/mouth thickness which is preferred by a sensory panel. Complex modulus is measured as described above. Shear stress is measured as described in example 3.

In a preferred embodiment the *Streptococcus thermophilus* strain DSM 33676 generates a shear stress that is at least 1% improved when compared to its mother strain, such as 2%, e.g. 3%, such as 4%, e.g. 5%, such as 6%, e.g. 7%, such as 8%, e.g. 9%, such as 10% when compared to its mother strain when measured at 300 1/s (Pa) after 16 hours of growth in skimmed milk (0.5% fat) at 43° C. when inoculated in an amount of at least $10^7$ cells per ml of milk.

In a preferred embodiment the *Streptococcus thermophilus* strain DSM 33676 generates a complex modulus that is at least 1% improved when compared to its mother strain, such as 2%, e.g. 3%, such as 4%, e.g. 5%, such as 6%, e.g. 7%, such as 8%, e.g. 9%, such as 10% when compared to its mother strain when measured by oscillation at 1.52 Hz after 16 hours of growth in in skimmed milk (0.5% fat) at 43° C. when inoculated in an amount of at least $10^7$ cells per ml of milk.

By "texture" or "mouthfeel" are meant the product's physical and chemical interaction in the mouth.

It has been unexpectedly found that mutants from *S. thermophilus* strains resistant towards tellurite salts as K2TeO3 are showing increased rheological properties. Thus, in one embodiment the *Streptococcus thermophilus* strain DSM 33676 is resistant to tellurite and/or salts or derivatives thereof.

Compositions

A further aspect of the present invention relates to a composition comprising or consisting of the *Streptococcus thermophilus* strain DSM 33676.

The composition of the present invention may be provided in several forms. It may be a frozen form, dried form, freeze dried form, or liquid form. Thus, in one embodiment the composition is in frozen, dried, freeze-dried or liquid form.

The composition of the present invention may additionally comprise cryoprotectants, lyoprotectants, antioxidants, nutrients, fillers, flavorants or mixtures thereof. The composition preferably comprises one or more of cryoprotectants, lyoprotectants, antioxidants and/or nutrients, more preferably cryoprotectants, lyoprotectants and/or antioxidants and most preferably cryoprotectants or lyoprotectants, or both. Use of protectants such as cryoprotectants and lyoprotectant are known to a skilled person in the art. Suitable cryoprotectants or lyoprotectants include mono-, di-, tri- and polysaccharides (such as glucose, mannose, xylose, lactose, sucrose, trehalose, raffinose, maltodextrin, starch and gum arabic (acacia) and the like), polyols (such as erythritol, glycerol, inositol, mannitol, sorbitol, threitol, xylitol and the like), amino acids (such as proline, glutamic acid), complex substances (such as skim milk, peptones, gelatin, yeast extract) and inorganic compounds (such as sodium tripolyphosphate). In one embodiment, the composition according to the present invention may comprise one or more cryoprotective agent(s) selected from the group consisting of inosine-5'-monophosphate (IMP), adenosine-5'-monophosphate (AMP), guanosine-5'-monophosphate (GMP), uranosine-(UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds. Suitable antioxidants include ascorbic acid, citric acid and salts thereof, gallates, cysteine, sorbitol, mannitol, maltose. Suitable nutrients include sugars, amino acids, fatty acids, minerals, trace elements, vitamins (such as vitamin B-family, vitamin C). The composition may optionally comprise further substances including fillers (such as lactose, maltodextrin) and/or flavorants.

In one embodiment of the invention the cryoprotective agent is an agent or mixture of agents, which in addition to its cryoprotectivity has a booster effect.

The expression "booster effect" is used to describe the situation wherein the cryoprotective agent confers an increased metabolic activity (booster effect) on to the thawed or reconstituted culture when it is inoculated into the medium to be fermented or converted. Viability and metabolic activity are not synonymous concepts. Commercial frozen or freeze-dried cultures may retain their viability, although they may have lost a significant portion of their metabolic activity e.g. cultures may lose their acid-producing (acidification) activity when kept stored even for shorter periods of time. Thus viability and booster effect has to be evaluated by different assays. Whereas viability is assessed by viability assays such as the determination of colony forming units, booster effect is assessed by quantifying the relevant metabolic activity of the thawed or reconstituted culture relative to the viability of the culture. The term "metabolic activity" refers to the oxygen removal activity of the cultures, its acid-producing activity, i.e. the production of e.g. lactic acid, acetic acid, formic acid and/or propionic acid, or its metabolite producing activity such as the production of aroma compounds such as acetaldehyde, (a-acetolactate, acetoin, diacetyl and 2,3-butylene glycol (butanediol)).

In one embodiment the composition of the invention contains or comprises from 0.2% to 20% of the cryoprotective agent or mixture of agents measured as % w/w of the material. It is, however, preferable to add the cryoprotective agent or mixture of agents at an amount which is in the range from 0.2% to 15%, from 0.2% to 10%, from 0.5% to 7%, and from 1% to 6% by weight, including within the range from 2% to 5% of the cryoprotective agent or mixture of agents measured as % w/w of the frozen material by weight. In a preferred embodiment the culture comprises approximately 3% of the cryoprotective agent or mixture of agents measured as % w/w of the material by weight. The amount of approximately 3% of the cryoprotective agent corresponds to concentrations in the 100 mM range. It should be recognized that for each aspect of embodiment of the invention the ranges may be increments of the described ranges.

In a further aspect, the composition of the present invention contains or comprises an ammonium salt (e.g. an ammonium salt of organic acid (such as ammonium formate and ammonium citrate) or an ammonium salt of an inorganic acid) as a booster (e.g. growth booster or acidification booster) for bacterial cells, such as cells belonging to the species *S. thermophilus*, e.g. (substantial) urease negative bacterial cells. The term "ammonium salt", "ammonium formate", etc., should be understood as a source of the salt or a combination of the ions. The term "source" of e.g. "ammonium formate" or "ammonium salt" refers to a compound or mix of compounds that when added to a culture of cells, provides ammonium formate or an ammonium salt. In some embodiments, the source of ammonium releases ammonium into a growth medium, while in other embodiments, the ammonium source is metabolized to produce ammonium. In some preferred embodiments, the ammonium source is exogenous. In some particularly preferred embodiments, ammonium is not provided by the dairy substrate. It should of course be understood that ammonia may be added instead of ammonium salt. Thus, the term ammonium salt comprises ammonia (NH3), NH4OH, NH4+, and the like.

In one embodiment the composition of the invention may comprise thickener and/or stabilizer, such as pectin (e.g. HM pectin, LM pectin), gelatin, CMC, Soya Bean Fiber/Soya Bean Polymer, starch, modified starch, carrageenan, alginate, and guar gum In one embodiment wherein the microorganism produces a polysaccharide (such as EPS) which causes a high/ropy texture in the acidified milk product the acidified milk product is produced substantially free, or completely free of any addition of thickener and/or stabilizer, such as pectin (e.g. HM pectin, LM pectin), gelatin, CMC, Soya Bean Fiber/Soya Bean Polymer, starch, modified starch, carrageenan, alginate, and guar gum. By substantially free should be understood that the product comprise from 0% to 20% (w/w) (e.g. from 0% to 10%, from 0% to 5% or from 0% to 2% or from 0% to 1%) thickener and/or stabilizer.

The composition may be a mixture or as a kit-of-parts comprising:
  i) the *Streptococcus thermophilus* strain DSM 33676, and
  ii) a strain belonging to the species *Lactobacillus delbrueckii* subsp *bulgaricus*.

In order to obtain the best combination of acidity, taste, texture of a product such as a dairy product, like yoghurt, a combination of *S. thermophilus* and *L. bulgaricus* is often applied.

In one embodiment the mixture or kit-of-parts may comprise *S. thermophilus* strain DSM 33676 in combination with *S. thermophilus* strain DSM 24011 and *L. bulgaricus* strain DSM 33571.

In another embodiment the mixture or kit-of-parts may comprise *S. thermophilus* strain DSM 33676 in combination with *S. thermophilus* strain DSM 24011 and *L. bulgaricus* strain DSM 24074.

Example 3 shows that a mixed culture comprising *S. thermophilus* and *L. bulgaricus*.

Probiotic Strains

The term "probiotic bacteria" refers to viable bacteria which are administered in adequate amounts to a consumer for the purpose of achieving a health-promoting effect in the consumer. Probiotic bacteria are capable of surviving the conditions of the gastrointestinal tract after ingestion and colonize the intestine of the consumer.

It will be appreciated that the *Lactobacillus* genus taxonomy was updated in 2020. The new taxonomy is disclosed in Zheng et al. 2020 and will be cohered to herein if nothing else is noticed. For the purpose of the present invention, table 1 presents a list of new and old names of some *Lactobacillus* species relevant to the present invention.

TABLE 1

New and old names of some *Lactobacillus* species relevant to the present invention

| Old Name | New Name |
| --- | --- |
| *Lactobacillus reuteri* | *Limosilactobacillus reuteri* |
| *Lactobacillus rhamnosus* | *Lacticaseibacillus rhamnosus* |
| *Lactobacillus salivarius* | *Ligilactobacillus salivarius* |
| *Lactobacillus casei* | *Lacticaseibacillus casei* |
| *Lactobacillus paracasei* subsp. *paracasei* | *Lacticaseibacillus paracasei* subsp. *Paracasei* |
| *Lactobacillus plantarum* subsp. *plantarum* | *Lactiplantibacillus plantarum* subsp. *plantarum* |
| *Lactobacillus fermentum* | *Limosilactobacillus fermentum* |
| *Lactobacillus animalis* | *Ligilactobacillus animalis* |
| *Lactobacillus buchneri* | *Lentilactobacillus buchneri* |
| *Lactobacillus curvatus* | *Latilactobacillus curvatus* |
| *Lactobacillus futsaii* | *Companilactobacillus futsaii* |
| *Lactobacillus sakei* subsp. *sakei* | *Latilactobacillus sakei* subsp. |
| *Lactobacillus pentosus* | *Lactiplantibacillus pentosus* |

In a particular embodiment of the invention the probiotic strain according to the present invention is selected from the group consisting of bacteria of the genus *Lactobacillus*, such as *Lactobacillus acidophilus*, *Lacticaseibacillus paracasei*, *Lacticaseibacillus rhamnosus*, *Lacticaseibacillus casei*, *Lactobacillus delbrueckii*, *Lactobacillus lactis*, *Lactiplantibacillus plantarum*, *Limosilactobacillus reuteri* and *Lactobacillus johnsonii*, the genus *Bifidobacterium*, such as the *Bifidobacterium longum*, *Bifidobacterium adolescentis*, *Bifidobacterium bifidum*, *Bifidobacterium breve*, *Bifidobacterium animalis* subsp. *lactis*, *Bifidobacterium dentium*, *Bifidobacterium catenulatum*, *Bifidobacterium angulatum*, *Bifidobacterium magnum*, *Bifidobacterium pseudocatenulatum* and *Bifidobacterium infantis*, and the like.

In a particular embodiment of the invention, the probiotic *Lactobacillus* strain is selected from the group consisting of *Lactobacillus acidophilus*, *Lacticaseibacillus paracasei*, *Lacticaseibacillus rhamnosus*, *Lactobacillus* casei, *Lactobacillus delbrueckii*, *Lactobacillus lactis*, *Lactiplantibacillus plantarum*, *Limosilactobacillus reuteri* and *Lactobacillus johnsonii*.

In a particular embodiment of the invention, the probiotic *Lactobacillus* strain is selected from the group consisting of a *Lacticaseibacillus rhamnosus* strain and a *Lacticaseibacillus paracasei* strain.

In a particular embodiment of the invention, the probiotic strain is *Lacticaseibacillus rhamnosus* strain LGG® deposited as ATCC53103.

In a particular embodiment of the invention, the probiotic strain is *Lacticaseibacillus paracasei* strain CRL 431 deposited as ATCC55544.

In a particular embodiment of the invention, the probiotic *Bifidobacterium* strain is selected from the group consisting of *Bifidobacterium longum*, *Bifidobacterium adolescentis*, *Bifidobacterium bifidum*, *Bifidobacterium breve*, *Bifidobacterium animalis* subsp. *lactis*, *Bifidobacterium dentium*, *Bifidobacterium catenulatum*, *Bifidobacterium angulatum*, *Bifidobacterium magnum*, *Bifidobacterium pseudocatenulatum* and *Bifidobacterium infantis*.

In a particular embodiment of the invention, the probiotic *Bifidobacterium* probiotic strain is *Bifidobacterium animalis* subsp. *lactis* BB-12 deposited as DSM15954.

The above mixtures or kit-of-parts may be further combined with other lactic acid bacteria such as but not limited to probiotic bacteria. In one embodiment the at least one lactic acid bacteria is selected from the group consisting of *Bifidobacterium* such as *Bifidobacterium animalis* subsp. *Lactis* (e.g. BB-12®),
*Lactobacillus acidophilus*)(LA-5®, *Lacticaseibacillus rhamnosus* (e.g. LGG®) and combinations thereof. Which *Bifidobacterium*,
*Lactobacillus acidophilus* and/or *Lacticaseibacillus rhamnosus* to apply depending on their application and food to be produced.

In one embodiment the mixture or kit-of-parts may comprise *Streptococcus thermophilus* strain DSM 33676 in combination with *Streptococcus thermophilus* strain DSM 24011, *Lactobacillus delbrueckii* subsp *bulgaricus* strain DSM 33571 and *Bifidobacterium animalis* subsp. *Lactis* strain DSM 33443.

In one embodiment the mixture or kit-of-parts may comprise *S. thermophilus* strain DSM 33676 in combination with *S. thermophilus* strain DSM 24011, *Lactobacillus delbrueckii* subsp *bulgaricus* strain DSM 24074 and *Bifidobacterium animalis* subsp. *Lactis* strain DSM 33443.

In one embodiment the mixture or kit-of-parts may comprise *S. thermophilus* strain DSM 33676 in combination with *S. thermophilus* strain DSM 24011, *Lactobacillus delbrueckii* subsp *bulgaricus* strain DSM 33571, *Bifidobacterium animalis* subsp. *Lactis* strain DSM 33443 and *Lactobacillus acidophilus* strain DSM 13241.

In one embodiment the mixture or kit-of-parts may comprise *S. thermophilus* strain DSM 33676 in combination with *S. thermophilus* strain DSM 24011, *Lactobacillus delbrueckii* subsp *bulgaricus* strain DSM 24074, *Bifidobacterium animalis* subsp. *Lactis* strain DSM 33443 and *Lactobacillus acidophilus* strain DSM 13241.

In one embodiment the mixture or kit-of-parts may comprise *S. thermophilus* strain DSM 33676 in combination with *S. thermophilus* strain DSM 24011, *Lactobacillus delbrueckii* subsp *bulgaricus* strain DSM 33571 and *Lacticaseibacillus rhamnosus* strain DSM 33156.

In one embodiment the mixture or kit-of-parts may comprise *S. thermophilus* strain DSM 33676 in combination with *S. thermophilus* strain DSM 24011, *Lactobacillus delbrueckii* subsp *bulgaricus* strain DSM 24074 and *Lacticaseibacillus rhamnosus* strain DSM 33156.

The above mixture or kit-of-parts may be further combined with other *S. thermophilus* strains. These strains may for example be DSM 32823 and/or DSM 32587.

The expression "mixture" means that the *S. thermophilus* strain(s) and the *Lactobacillus delbrueckii* subsp *bulgaricus* strain(s) are physically mixed together. In an embodiment, the *S. thermophilus* strain(s) and the *Lactobacillus delbrueckii* subsp *bulgaricus* strain(s) are in the same box or in the same pouch.

In contrast, the expression "A kit-of-part" comprising *S. thermophilus* strain(s) and the *L. bulgaricus* strain means that the culture of the *S. thermophilus* strain(s) and the *L. bulgaricus* strain(s) culture are physically separated but intended to be used together. Thus, the culture of the *S. thermophilus* strain(s) and the *L. bulgaricus* strain(s) culture are in different boxes or sachets. In an embodiment, the culture of the *S. thermophilus* strain(s) and the *L. bulgaricus* strain(s) are under the same format, i.e., are in a frozen format, in the form of pellets or frozen pellets, a powder form, such as a dried or freeze-dried powder.

In a particular embodiment of the present invention, the composition comprises from $10^4$ to $10^{12}$ CFU (colony forming units)/g of the *S. thermophilus* strain, such as from $10^5$ to $10^{11}$ CFU/g, such as from $10^6$ to $10^{10}$ CFU/g, or such as from $10^7$ to $10^9$ CFU/g of the *S. thermophilus* strain.

In a particular embodiment the composition further comprises from $10^4$ to $10^{12}$ CFU/g of the *L. bulgaricus* strain, such as from $10^5$ to $10^{11}$ CFU/g, such as from $10^6$ to $10^{10}$ CFU/g, or such as from $10^7$ to $10^9$ CFU/g of the *L. bulgaricus* strain.

*L. bulgaricus*, *S. thermophilus* and other lactic acid bacteria are commonly used as starter cultures serving a technological purpose in the production of various foods, such as in the dairy industry, such as for fermented milk products. Thus, in another preferred embodiment the composition is suitable as a starter culture.

The composition may be a starter culture such as a yoghurt starter culture.

The composition and/or starter culture may be frozen, spray-dried, freeze-dried, vacuum-dried, air dried, tray dried or in liquid form. Typically, the storage stability of the composition and/or starter culture can be extended by formulating the product with low water activity. By controlling the water activity (Aw), it is possible to predict and regulate the effect of moisture migration on the product. Therefore, it may be preferred that the water activity (Aw) of the dried compositions herein is in the range from 0.01-0.8, preferably in the range from 0.05-0.4.

A further aspect of the present invention relates to a method of producing a fermented product, comprising fermenting a substrate with the *Streptococcus thermophilus* strain DSM 33676 or a composition according to the present invention.

Depending on the product to be produced the substrate may be a milk substrate. A milk substrate is particularly preferred when fermented milk products such as yoghurt, buttermilk or kefir is the final product.

The milk substrate may be an animal or plant derived product. Thus, in an embodiment the fermented product is a dairy product. The dairy product may be selected from the group consisting of a fermented milk product such as but not limited to yoghurt, buttermilk and kefir or cheese such as but not limited to fresh cheese or pasta filata.

Even though the fermented product and/or the dairy product itself comprise acid and flavor generated during fermentation it may be desired that fermented product and/or the dairy product comprises an ingredient selected from the group consisting of a fruit concentrate, a syrup, a probiotic bacterial strain or culture, a coloring agent, a thickening agent, a flavoring agent, a preserving agent and mixtures thereof.

Likewise an enzyme may be added to the substrate e.g. the milk substrate before, during and/or after the fermenting, the enzyme being selected from the group consisting of an enzyme able to crosslink proteins, transglutaminase, an aspartic protease, chymosin, rennet and mixtures thereof.

In one embodiment the fermented product may be in the form of a stirred type product, a set type product or a drinkable product.

Clearly another aspect of the present invention relates to a fermented product obtainable by the method of the present invention. An aspect of the present invention is therefore also a fermented product comprising the *Streptococcus thermophilus* strain DSM 33676. The fermented product may be a dairy product.

A last aspect of the present invention relates to the use of the *Streptococcus thermophilus* strain DSM 33676 for the manufacture of a fermented product. Again the fermented product may be a dairy product.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The listing or discussion of an apparently prior published document in this specification should not necessarily be taken as an acknowledgement that the document is part of the state of the art or is common general knowledge.

Preferences, options and embodiments for a given aspect, feature or parameter of the invention should, unless the context indicates otherwise, be regarded as having been disclosed in combination with any and all preferences, options and embodiments for all other aspects, features and parameters of the invention. This is especially true for the description of the microencapsulated microbial culture and all its features, which may readily be part of the final composition obtained by the method as described herein. Embodiments and features of the present invention are also outlined in the following items and also illustrated by the following non-limiting examples.

Deposits and Expert Solutions

The *Streptococcus thermophilus* strain were deposited at DSMZ (Deutsche Sammlung von Mikroorganismen and Zellkulturen GmbH, Inhoffenstr. 7B, D-38124 Braunschweig, Germany) under the accession number DSM 33676 on 29 Oct. 2020 by Chr. Hansen A/S, Hoersholm, Denmark.

The applicant requests that a sample of the deposited microorganisms stated below may only be made available to an expert, until the date on which the patent is granted.

TABLE 2

| Deposits made at a Depositary institution having acquired the status of international depositary authority under the Budapest Treaty on the International Recognition of the Deposit of Microorganisms for the Purposes of Patent Procedure: *Leibniz Institute DSMZ-German Collection of Microorganisms and Cell Cultures* Inhoffenstr. 7B, 38124 Braunschweig, Germany. | | |
| --- | --- | --- |
| Strain | Accession No. | Deposit date |
| *Streptococcus thermophilus* | DSM 33676 | 2020 Oct. 29 |

Items

X1. *Streptococcus thermophilus* strain DSM 33676 and mutants and variants thereof.

X2. The *Streptococcus thermophilus* strain DSM 33676 according to item X1, wherein the mutants and variants show the same or similar shear stress and/or gel firmness characteristics as DSM 33676.

X3. The *Streptococcus thermophilus* strain DSM 33676 according to any one of items X1-X2, wherein said stain is resistant to Tellurite and/or salts or derivatives thereof.

Y1. A composition comprising the *Streptococcus thermophilus* strain DSM 33676 according to of any of items X1-X3.

Y2. The composition according to item Y1 comprising, either as a mixture or as a kit-of-parts comprising:
   i) the *Streptococcus thermophilus* strain DSM 33676 according to any one of items X1-X3; and
   ii) a strain belonging to the species *Lactobacillus delbrueckii* subsp *bulgaricus.*

Y3. The composition according to any of items Y1-Y2, wherein the composition is a starter culture.

Y4. The composition according to any of items Y1-Y3, wherein the composition and/or starter culture is in frozen, spray-dried, freeze-dried, vacuum-dried, air dried, tray dried or liquid form.

Z1. A method of producing a fermented product, comprising fermenting a substrate with the *Streptococcus ther-*

13

14

*mophilus* strain DSM 33676 according to any one of items X1-X3, or a composition of any of items Y1-Y4.

Z2. The method according to item Z1, wherein the substrate is a milk substrate.

Z3. The method according to any one of items Z1-Z2, wherein the milk substrate is an animal or plant derived product.

Z4. The method according to any one of items Z1-Z3, wherein the fermented product is a dairy product.

Z5. The method according to item Z4, wherein the dairy product is selected from the group consisting of a fermented milk product (e.g. yoghurt, buttermilk or kefir) or a cheese (e.g. fresh cheese or pasta filata)

Z6. The method according to any one of items Z4-Z5, wherein the fermented product further comprises an ingredient selected from the group consisting of a fruit concentrate, a syrup, a probiotic bacterial strain or culture, a coloring agent, a thickening agent, a flavoring agent, a preserving agent and mixtures thereof.

Z7. The method according to item Z6, wherein an enzyme is added to the substrate before, during and/or after the fermenting, the enzyme being selected from the group consisting of an enzyme able to crosslink proteins, transglutaminase, an aspartic protease, chymosin, rennet and mixtures thereof.

Z8. The method according to any one of items Z1-Z7, wherein the fermented product is in the form of a stirred type product, a set type product, or a drinkable product.

Q1. A fermented product obtainable by the method of item Z1.

Q2. The fermented product according to item Q1, wherein the fermented product is a dairy product.

P1. A fermented product comprising the *Streptococcus thermophilus* strain DSM 33676 according to of any of items X1-X3.

P2. The fermented product according to item P1, wherein the fermented product is a dairy product.

W1. Use of the *Streptococcus thermophilus* strain DSM 33676 according to of any one of items X1-X3 for the manufacture of a fermented product.

W2. The use according to item W1, wherein the fermented product is a dairy product.

EXAMPLES

Example 1: Isolation of Tellurite Resistant Mutants from *S. thermophilus* DSM 18111 with Increased Texturing Properties Tellurite resistant mutants were isolated from DSM 18111 (also termed "mother strain") as follows.

The mutants were directly screened on M17 agar plates containing 0.1 mM K2Te03 by plating over night cultures of DSM 18111 on those plates, followed by incubation at 37° C. for 1 to 3 days. A number of fifteen mutants was purified on M17 agar plates containing 0.1 mM K2Te03 demonstrating a stable tellurite resistant phenotype. One of the tellurite mutants showing a tellurite resistance phenotype was named DSM 33676.

Mutants of DSM 18111 were inoculated from an M17 overnight culture containing 0.1 mM K2Te03 1% in milk, and incubated at 37° C. for 24 hours. The viscosity of the fermented milk was then determined by measuring efflux time from a 25 ml pipette. The longer the efflux time the higher is the viscosity of the test medium. The efflux time was determined as an average of three measurements.

The efflux time, i.e. the viscosity, was increased for the tellurite resistant mutants. For mutant DSM 33767 an increase of viscosity was measured with 20% compared to the mother strain DSM 18111.

With this experiment it was demonstrated that it is possible to increase the texturing properties of eps positive *S. thermophilus* strains further by the isolation of tellurite resistant mutants.

Example 2: Comparison Between Mother Stain DSM 18111 and DSM 33676 on Shear Stress and Complex Modulus DSM 18111 was inoculated in 9.5% reconstituted skimmed milk and incubated at 43° C. to generate an over night culture. DSM 18111 was then inoculated in duplicates from the milk over night culture 1% in skimmed milk (0.5% fat) and incubated at 41° C. for 16 hours. Likewise DSM 33676 was inoculated from the milk over night culture 1% in skimmed milk (0.5%) and incubated at 43° C. for 16 hours.

The day after incubation, the fermented milk was brought to 13° C. and stirred gently by means of a stick fitted with a bored disc until homogeneity of the sample. The rheological properties of the sample were assessed on a rheometer (StressTech, Reologica Instruments, Sweden) equipped with a C25 coaxial measuring system.

The viscometry test was made with shear rates varying from 0.27 to 300 1/s in 21 steps. Shear rates were increased and then decreased and the upward and downward curves of shear stress and apparent viscosity were recorded.

Delay and integration times were 5 s and 10 s, respectively. For further analysis, shear stress at 300 s$-1$ was chosen.

Results

Single Strain Results:

TABLE 3

Shear Stress, Complex Modulus and Ratio performance of mother strain (DSM 18111) and mutant strain (DSM 33676)

| Sample name | Shear Stress | Complex Modulus | Ratio |
|---|---|---|---|
| DSM 18111 | 32.9 | 79.2 | 0.502 |
| DSM 18111 | 33.7 | 88.8 | 0.509 |
| DSM 33676 | 30.8 | 90.9 | 0.511 |
| DSM 33676 | 30.8 | 90.9 | 0.51 |

DSM 33676 showed increased gel firmness (complex modulus) by 8% compared with DSM 18111 (average from two measurements).

Mixed Culture Results:

Selection of mutant DSM 33676 for upscaling was conducted using reduced protein (3%) skim milk, heat treated for 5 min at 95° C. and cooled to fermentation temperature before use. The inoculation material was overnight culturing of the candidates in sterile milk added yeast extract. The mutant DSM 33676 was compared to an already industrialized improved strain from the same family (DSM 22935).

All mutants were tested in the background cultures, consisting of 50% of the strain to be tested, 10% of acidifying *S. thermophilus,* 30% of texturing *S. thermophilus* and 10% *L. bulgaricus* resulting to 12 different variations for each mutant. Resistance during aspiration by a Hamilton robot (TADM) was measured to check for increased viscosity. The averaged results for each mutant were compared to the average with the reference strain. The more negative the pressure (mPa) during aspiration gets, the higher the viscosity of the sample Results can be seen in the following table:

TABLE 4 pressure drop during aspiration for mixtures comprising DSM 33676 and DSM 22935 respectively.

| | Pressure drop during aspiration From | Pressure drop during aspiration From |
|---|---|---|
| Mix comprising DSM 33676 | −1500 mPa | −2100 mPa |
| Mix comprising DSM 22935 | −1500 mPa | −1780 mPa |

Example 3: Production of Plain Stirred Yogurt with a Blend Comprising DSM 33676

Materials and Methods

Milk base: 4.0% protein, 1.5% fat. Fresh milk with Arla Medium Heat Skimmed milk powder (SMP).

Cultures: Culture 1 (*L. bulgaricus* strain DSM 33571, *S. thermophilus* stains DSM 24011 and DSM 33676), and F-DVS YoFlex® Premium 1.0, a proprietary prior art culture comprising one *L. bulgaricus* strain in combination with 2 different *S. thermophilus* strains.

| | |
|---|---|
| Fermentation scale | 3 L |
| Mixing of powder and rehydration of milk base | Disperse powder in cold milk (<10° C.), heat to 58° C. (±2° C.) and re-hydrate for 1 hour at 58° C. (±2° C.) with stirring |
| Homogenization | 200/50 bar at 65° C. |
| Pasteurization | 95° C. for 5 min |
| Culture inoculation | 500 U/2500 L (min. 1E10 cfu/g), inoculation at 43° C. |
| Fermentation temperature | 43° C. |
| Cut pH | pH 4.55 |
| Post treatment | Apply 2 bar before plate heat exchanger with outlet temperature set to 20° C. (±2° C.) |

Results
Complex Modulus G*—Correlating to Gel Firmness

Complex Modulus G* is evaluated by oscillation measurement using ASC rheometer model DSR502 from Anton Paar. The method is based on an oscillation step, where the sample is oscillated between two surfaces, with the upper geometry (bob) moving and the lower cup remaining stationary. The oscillation is performed from 0.5-8 Hz at constant strain. For these evaluations the results are extracted from measurements at 1.52 Hz. Samples are placed at 13° C. for 1 hour prior to measuring. Each sample is gently stirred with a spoon 5 times from bottom to top to assure a homogenous sample. The rheology cups are filled until the line and placed in the sample magazine. Samples are measured in duplicates using two separate yogurt cups. Measurements are conducted at day +7 and temperature of measurement is set to 13° C. Samples are stored at 5° C. until the day of measurement. As there are three productions included for these results there is in total 6 data points.

TABLE 5

Gel firmness results measured by Complex Modulus G* by Oscillation at 1.52 Hz. The results are shown as average results, including the standard deviation from 3 replicate trials in ATC. Measurements were conducted at day +7 adjusting the temperature to 13° C.

| Culture | Average results Complex Modulus G* at 1.52 Hz (Pa) n = 6 | STDev |
|---|---|---|
| F-DVS YoFlex ® Premium 1.0 | 143.5 | 7.1 |
| Culture 1 | 140.8 | 7.0 |

Shear Stress—Correlating to Mouth Thickness

Shear stress is measured by using ASC rheometer model DSR502 from Anton Paar. The method is using a rotational step which is based on a rotational deformation on the sample, from 10-3 s−1 to 300 s−1, and then back to 10-3 s−1. The corresponding shear stress is measured. For these results, four shear rates (0.3; 30; 135; 300 s−1) are extracted from the flow curve (see Table 4). Samples are placed at 13° C. for 1 hour prior to measuring. Each sample is gently stirred with a spoon 5 times from bottom to top to assure a homogenous sample. The rheology cups are filled until the line and placed in the sample magazine. Samples are measured in duplicates using two separate yogurt cups. Measurements are conducted at day +7 and temperature of measurement is set to 13° C. Samples are stored at 5° C. until the day of measurement.

TABLE 6

Shear stress results measured by Anton Paar rheometer. The results are shown as average results, including the standard deviation from 3 replicate trials in ATC. Measurements were conducted at day +7 adjusting the temperature to 13° C.

| Culture | 0.3 s−1 | 30 s−1 | 135 s−1 | 300 s−1 |
|---|---|---|---|---|
| | AVERAGE | | | |
| F-DVS YoFlex ® Premium 1.0 | 4.8 | 25.7 | 47.9 | 54.2 |
| Culture 1 | 4.9 | 32.1 | 54.3 | 57.1 |
| | STD | | | |
| F-DVS YoFlex ® Premium 1.0 | 0.2 | 1.3 | 0.8 | 0.7 |
| Culture 1 | 0.3 | 1.8 | 1.3 | 0.7 |

The invention claimed is:

1. A strain of *Streptococcus thermophilus* deposited at Deutsche Sammlung von Mikroorganismen und Zellkulturen GmbH (Braunschweig, Germany) (DSMZ) under accession number DSM 33676 and mutants derived therefrom, wherein the deposited strain is resistant to tellurite and/or salts or derivatives thereof and wherein mutants are obtained by using the deposited strain as a mother strain, wherein the mutant strain has the same or higher resistance to tellurite and/or salts or derivatives thereof as compared to the deposited strain.

2. The *Streptococcus thermophilus* strain according to claim 1, wherein the strain is a mutant of strain DMS 33676 that exhibits shear stress characteristics or gel firmness characteristics that are substantially the same or improved compared to DSM 33676.

3. A composition comprising the *Streptococcus thermophilus* strain according to claim 1.

4. The composition according to claim 3, further comprising a strain of *Lactobacillus delbrueckii* subsp. *bulgaricus*.

5. The composition according to claim 3, wherein the composition is a starter culture.

6. The composition according to claim 3, wherein the composition is in frozen, spray-dried, freeze-dried, vacuum-dried, air dried, tray dried, or liquid form.

7. A method of producing a fermented product, comprising fermenting a substrate with the mutant *Streptococcus thermophilus* strain according to claim 1.

8. The method according to claim 7, wherein the substrate is a milk substrate.

9. The method according to claim 7, wherein the fermented product is a dairy product.

10. The method according to claim 7, wherein the fermented product further comprises one or more ingredients selected from a fruit concentrate, a syrup, a probiotic bacterial culture, a coloring agent, a thickening agent, a flavoring agent, and a preserving agent.

11. The method according to claim 7, further comprising adding an enzyme to the substrate before, during, and/or after the fermenting, the enzyme being one or more selected from the group consisting of an enzyme able to crosslink proteins, transglutaminase, an aspartic protease, chymosin, and rennet.

12. A fermented product obtained by the method according to claim 7.

13. A fermented product comprising the *Streptococcus thermophilus* strain according to claim 1.

14. The *Streptococcus thermophilus* strain according to claim 1, wherein the strain is *Streptococcus thermophilus* strain DSM 33676.

15. The composition according to claim 3, wherein the *Streptococcus thermophilus* strain is *Streptococcus thermophilus* strain DSM 33676.

16. The method according to claim 7, wherein the *Streptococcus thermophilus* strain is *Streptococcus thermophilus* strain DSM 33676.

17. A product comprising as a kit-of-parts
   (i) the *Streptococcus thermophilus* strain according to claim 1; and
   (ii) a strain of *Lactobacillus delbrueckii* subsp *bulgaricus*.

18. The product according to claim 17, wherein the *Streptococcus thermophilus* strain is *Streptococcus thermophilus* strain DSM 33676.

19. The composition of claim 3, further comprising a cryoprotectant.

20. The composition of claim 19, wherein the cryoprotectant has a booster effect.

\* \* \* \* \*